US005809152A

United States Patent [19]

Nakamura et al.

[11] Patent Number: 5,809,152

[45] Date of Patent: Sep. 15, 1998

[54] APPARATUS FOR REDUCING NOISE IN A CLOSED SPACE HAVING DIVERGENCE DETECTOR

[75] Inventors: Mitsuru Nakamura, Hitachinaka; Noriharu Sato, Tokyo; Mitsuhide Sasaki; Hiroyuki Saito, both of Hitachinaka; Toshiyuki Tabata, Sagamihara; Satoshi Hasegawa, Yamato, all of Japan

[73] Assignees: Hitachi, Ltd., Tokyo; Nissan Motor Co., Ltd., Kanagawa, both of Japan

[21] Appl. No.: 728,640

[22] Filed: Oct. 10, 1996

Related U.S. Application Data

[63] Continuation-in-part of Ser. No. 589,575, Jan. 22, 1996, abandoned, which is a continuation of Ser. No. 907,288, Jul. 1, 1992, which is a continuation-in-part of Ser. No. 53,393, Apr. 28, 1993, abandoned.

[30] Foreign Application Priority Data

| | | | |
|---|---|---|---|
| Jul. 11, 1991 | [JP] | Japan | 3-171054 |
| Apr. 28, 1992 | [JP] | Japan | 4-109992 |

[51] Int. Cl.$^{6}$ .......... A61F 11/26
[52] U.S. Cl. .......... 381/71.8; 381/71.1
[58] Field of Search .......... 381/71.4, 71.8, 381/71.11, 71.12, 71.1, 94.1

[56] References Cited

U.S. PATENT DOCUMENTS

| | | | |
|---|---|---|---|
| 5,018,202 | 5/1991 | Takahashi et al. | 381/71.8 |
| 5,029,218 | 7/1991 | Nagayasu | 381/71.8 |
| 5,251,262 | 10/1993 | Suzuki et al. | 381/71.8 |
| 5,426,703 | 6/1995 | Hamabe et al. | 381/71.8 |

FOREIGN PATENT DOCUMENTS

| | | | |
|---|---|---|---|
| 0465172 | 1/1992 | European Pat. Off. | 381/71 |
| 4011291 | 1/1992 | Japan | 381/94 |
| 2 149 614 | 6/1985 | United Kingdom . | |

OTHER PUBLICATIONS

*IEEE Transactions on Acoustics, Speech, and Signal Processing* entitled A Multiple Error LMS Algorithm and Its Application to the Active Control of Sound and Vibration, vol. ASSP–35, No. 10, Oct. 1987.

*Primary Examiner*—Curtis A. Kuntz
*Assistant Examiner*—Ping W. Lee
*Attorney, Agent, or Firm*—Evenson, McKeown, Edwards & Lenahan, P.L.L.C.

[57] ABSTRACT

An automatic sound suppression system is automatically disengaged whenever noise in an area and generated counter noise deviate in their reverse phase relationship or if the amplitude of the counter noise deviates from that of the noise. The system can also be automatically disengaged whenever divergence prediction means predicts that sounds of the noise and the counter noise diverge or whenever divergence prediction means predict that sounds of the noise and the counter noise are about to diverge. The system can also operate as a vibration reducing apparatus which is also automatically disengaged whenever divergence prediction means predicts that a vibration and a generated countervibration diverge.

33 Claims, 8 Drawing Sheets

$\frac{ds}{dt}$ : TIME DIFFERENTIAL OF EFFECTIVE SOUND PRESSURE AT NOISE DETECTOR

APPARATUS FOR REDUCING NOISE IN A CLOSED SPACE HAVING DIVERGENCE DETECTOR

CROSS-REFERENCE TO RELATED APPLICATIONS

This application is a continuation-in-part of U.S. patent application Ser. No. 08/589,575, filed Jan. 22, 1996, now abandonded which is a continuation of U.S. patent application Ser. No. 07/907,288, now abandoned, filed Jul. 1, 1992, and it is a continuation-in-part of U.S. patent application Ser. No. 08/053,393, filed Apr. 28, 1993 now abandoned.

BACKGROUND OF THE INVENTION

A. The present invention relates to a noise-reducing apparatus for canceling out noises or the like generated by propagation of mechanical vibrations with sounds of the same amplitudes and reverse phases to reduce actively. More particularly, it relates to a noise-reducing apparatus that avoids increase of the noises if a muting effect cannot be made.

Noises are generated by mechanical vibrations propagating from an adjacent mechanical vibration source. Automobiles and ships have engines as periodical mechanical vibration sources, and vibrations generated on an airplane's wings, etc. act as periodic mechanical vibration sources. Frequencies of these noises can be determined since they depend on the mechanical vibration frequencies. However, often it cannot be determined where the cabins have resonant sources among the ceilings, floors, walls, windows, etc. which act as actual noise generating sources.

A conventional noise-reducing apparatus (FIG. 6) comprises a plurality of microphones 4 for detecting sound pressures at a plurality of positions in noise spaces, such as a cab and cabins, a plurality of speakers 5 for radiating secondary sounds to the noise space, and a controller 3 having a microprocessor 2 as an arithmetic device. If mechanical vibrations are propagated from an engine 1 to the cab and cabins, the vibrations generate noises in the cab. The microprocessor calculates the secondary sounds in terms of the mechanical vibration frequencies to actively cancel the noises out, taking into account a space acoustic transfer function of the noise spaces. The speakers 5 radiate the secondary sounds to the cab to reduce the noises in the cab. In operation, the microprocessor 2 calculates the secondary sounds to be radiated from the speakers 5 in a least mean squares algorithm (hereinafter referred to as the LMS algorithm), which is a type of steepest descent method, so as to minimize the remaining cab sounds detected by the microphones 4.

The noise-reducing apparatus described above is used such that its power supply is kept on for reducing the noises by the secondary sound radiations to always make the noise-reducing control function active. However, an adverse phenomenon occurs when the space acoustic transfer function between the microphones and speakers changes to a great extent during operation of the noise-reducing apparatus. If the atmospheric temperature changes abruptly, for example, its muting effect vanishes, which results in an increase of the noises by way of the secondary sound radiations. It is troublesome for a driver to turn off the apparatus whenever the noises increase. To make the use of noise-reducing apparatus prevalent, this problem needs to be solved.

B. This invention further relates to a noise-reducing apparatus which generates secondary sound whose amplitude is the same as but whose phase is opposite to that of noise occurring in a compartment of, for example, an automotive vehicle and in which this secondary sound is used to interfere with the noise so as to actively minimize the level of the noise. More particularly, this invention relates to a noise-reducing apparatus for actively reducing booming noise in a vehicle compartment, which detects an increase in the level of noise (referred to hereinafter as abnormal noise increase) resulting from deviation of the phase of the secondary sound from the state of 180 degree out-of-phase relative to the phase of the noise and which is therefore suitable for avoiding undesirable continuation of the state of abnormal noise increase.

A conventional noise-reducing apparatus is described 1n, for example, UK Patent Application GB 2 149 614 A. The disclosed conventional noise-reducing apparatus will be first described by reference to FIG. 6. This conventional noise-reducing apparatus is intended to be applied to a closed space, such as, a passenger compartment in an airplane or the like. Referring to FIG. 6, the conventional noise-reducing apparatus includes a plurality of loudspeakers 5 disposed in such a closed space, a plurality of microphones 4 disposed also in the closed space for measuring the sound pressure at predetermined positions in the compartment, measuring means for measuring a reference frequency of a sound input from a vibration source, such as, an engine 1, and a controller 3 containing a microprocessor 2. The sound pressure data measured by the microphones 4 are supplied to the microprocessor 2, together with the data of the reference frequency of the sound input from the engine 1, and, in the microprocessor 2, signals for driving the individual loudspeakers 5 are calculated or computed according to an algorithm applied to the method of least mean squares (referred to hereinafter as an LMS algorithm). This method is a kind of the steepest descent method commonly used for minimizing the sound pressure level in such a closed space. The loudspeaker drive signals provided by calculation or computation in the microprocessor 2 are supplied through amplifiers to the individual speakers 5 respectively, and secondary sound is generated from each of the loudspeakers 5 into the closed space so as to reduce or cancel the noise. In this case, the controller 3 controls the loudspeakers 5 so as to minimize the sum total of the sound pressure levels measured at the plural positions where the microphones 4 are disposed.

Consider now the case of an automotive vehicle of the four-cycle four-cylinder engine type which is a most typical one in these days. In the vehicle of this four-cycle four-cylinder engine type, the pistons, the connecting rods, etc. in the engine generally reciprocate at the same frequency as that of the engine combustion cycle. This reciprocating motion of the internal components of the engine leads to occurrence of an unbalanced force, and this unbalanced force acts to produce vibration of the engine 1, that is, to generate an exciting force, thereby generating noise in the vehicle compartment. This noise is felt as if it were confined in the vehicle compartment and is thus commonly called booming noise. Because the frequency of this noise is the same as the engine combustion cycle (that is, the reference input frequency described above), the noise occurs two times in one rotation of the crankshaft. That is, the frequency of the noise is two times the rotational frequency of the crankshaft. The rotation speed range commonly used in a modern high performance engine is about 600 rpm to 7500 rpm, and the corresponding frequency range of the noise is between 20 Hz and 250 Hz. This frequency range includes a frequency or frequencies which especially lead to the problem of resonance in the vehicle compartment.

SUMMARY OF THE INVENTION

A. Accordingly, an object of the present invention is to provide a noise-reducing apparatus with which the noises will not be increased by the secondary sound radiations due to a large change of the space acoustic transfer function in the noise spaces.

Briefly, the foregoing object is accomplished in accordance with aspects of the present invention by a noise-reducing apparatus. This comprises in combination: a noise detection device for detecting noises generated by propagation of mechanical vibration, an arithmetic device for calculating secondary sounds of the same amplitude as and phase reverse to the noises in terms of frequencies of the mechanical vibrations, a secondary sound generating device for generating the secondary sounds calculated by the arithmetic device to reduce the noises, a divergence prediction device for predicting whether remaining sounds of the noises and the secondary sounds diverge or not, and a function interruption device for automatically interrupting function of the control device if the divergence prediction device predicts divergence of the remaining sounds.

A feature of the present invention is that the noise-reducing apparatus does not need to be turned on or off by hand as the function interruption device can automatically interrupt the noise-reducing control whenever the noises due to the secondary sound radiations are predicted to increase. Another feature of the present invention is that the function interruption device does not wait to turn off the noise-reducing control after the noises have actually increased, but rather predicts the noise increase to interrupt before an actual noise increase. An uncomfortable feeling is therefore not caused by the noise increase.

B. The magnitude of the booming noise is determined by both the shape of the vehicle compartment and the value of the exciting force, and the magnitude of the booming noise has a periodical property. Thus, when the transfer function of the control system is properly modeled, it can be said that this booming noise is a subject that can be relatively stably controlled. However, when the space acoustic transfer function between the microphones and the loudspeakers disposed in the vehicle compartment changes greatly due to, for example, secular changes in the characteristics of the loudspeakers and microphones, the operation of the control system tends to become extremely unstable. In such a case, the manner of control according to the prior art LMS algorithm tends to give rise to such a problem that the controlled signals do not act to converge the sum of the least squares of the sound pressures to a minimum, and not only the ideal noise-reducing effect cannot be exhibited, but also the noise rather increases to the state of abnormal noise increase, as described in a paper entitled "A Multiple Error LMS Algorithm and Its Application to the Active Control of Sound and Vibration", IEEE Transactions on Acoustics, Speech, and Signal Processing, Vol. ASSP-35, No. 10, October 1987. When the state of abnormal noise increase occurs, the level of the control sound (the secondary sound) greatly increases to the extent that continuous generation of this very loud control sound over a large length of time leads to such an adverse effect that the occupants of the vehicle compartment will feel very uncomfortable. In such a case, it is desirable to stop the noise-reducing control as soon as possible. For this purpose, it is necessary to detect occurrence of the state of abnormal noise increase as quickly as possible. However, when a momentary increase in the level of the secondary sound is mistaken as occurrence of undesirable abnormal noise increase, and the noise-reducing control is frequently stopped, the noise-reducing apparatus itself mounted in the vehicle will be quite wasteful.

It is an object of the present invention to provide an active noise-reducing apparatus capable of reliably detecting occurrence of the state of undesirable abnormal noise increase.

According to one aspect of the present invention which attain the above object, the value of filter output power calculated on the basis of filter coefficients of an adaptive digital filter determining the level of secondary sound is continuously measured, and, when the total sum of time periods for which the measured value exceeds a pre-set threshold is equal to or exceeds a predetermined time, the apparatus detects occurrence of the state of abnormal noise increase.

According to another aspect of the present invention which attains the above object, the filter output power is sampled at intervals of a predetermined sampling period, and, when the number of these sampled values exceeding the pre-set threshold is equal to or exceeds a predetermined number of times, the apparatus detects occurrence of the state of abnormal noise increase.

According to still another aspect of the present invention which attains the above object, the apparatus detects occurrence of the state of abnormal noise increase when the value of the filter output power continues to exceed the threshold over a predetermined period of time.

According to yet another aspect of the present invention which attains the above object, the apparatus detects occurrence of the state of abnormal noise increase when the ratio of the total sum of time periods for which the filter output power exceeds a predetermined fixed period of time is equal to or more than a set value.

Because the magnitude of the booming noise is dependent on both the shape of the vehicle compartment and the level of the exciting force of the engine, the level of the magnitude of the noise can be generally predicted beforehand according to the type of the vehicle. Therefore, the maximum value of the level of the secondary sound used for the noise-reducing control purpose has a magnitude that can be generally predicted, too. Thus, occurrence of the state of abnormal noise increase can be monitored by detecting whether or not the value of the filter output power exceeds the threshold. However, it is necessary to exclude the phenomenon that the value of the filter output power momentarily exceeds the threshold. Various means as described above are provided so as to exclude such a problem. According to the present invention, even when the noise-reducing control is not properly effected, resulting in occurrence of the state of undesirable abnormal noise increase where the level of the secondary sound is quite higher than that of the noise, such a phenomenon can be quickly detected.

Other objects, advantages and novel features of the present invention will become apparent from the following detailed description of the invention when considered in conjunction with the accompanying drawings.

DETAILED DESCRIPTION OF THE DRAWINGS

A. The following describes an embodiment of the present invention by reference to the accompanying drawings. In machines having power sources, such as an internal-combustion engine, a piston, rod, and associated parts in the power source are generally reciprocated at the same frequency as the fuel cycle of the power source. These rotate the power source drive shaft. As their reciprocal motions are unbalanced forces, these motions are propagated to other portions of the machine as mechanical vibrations of the power source. These causes noises at the propagation portions. The noise frequency is the same as the fuel cycles per second of the power source, or two times the rotational frequency of the drive shaft. For a machine having a modern high performance engine, the ordinary rotational frequency of its engine is 600 to 7,500 rpm. The noise frequency is 20 to 250 Hz. If the mechanical vibration is propagated to portions that resonate in the range of the frequencies, the noises become particularly high.

Figure 1:
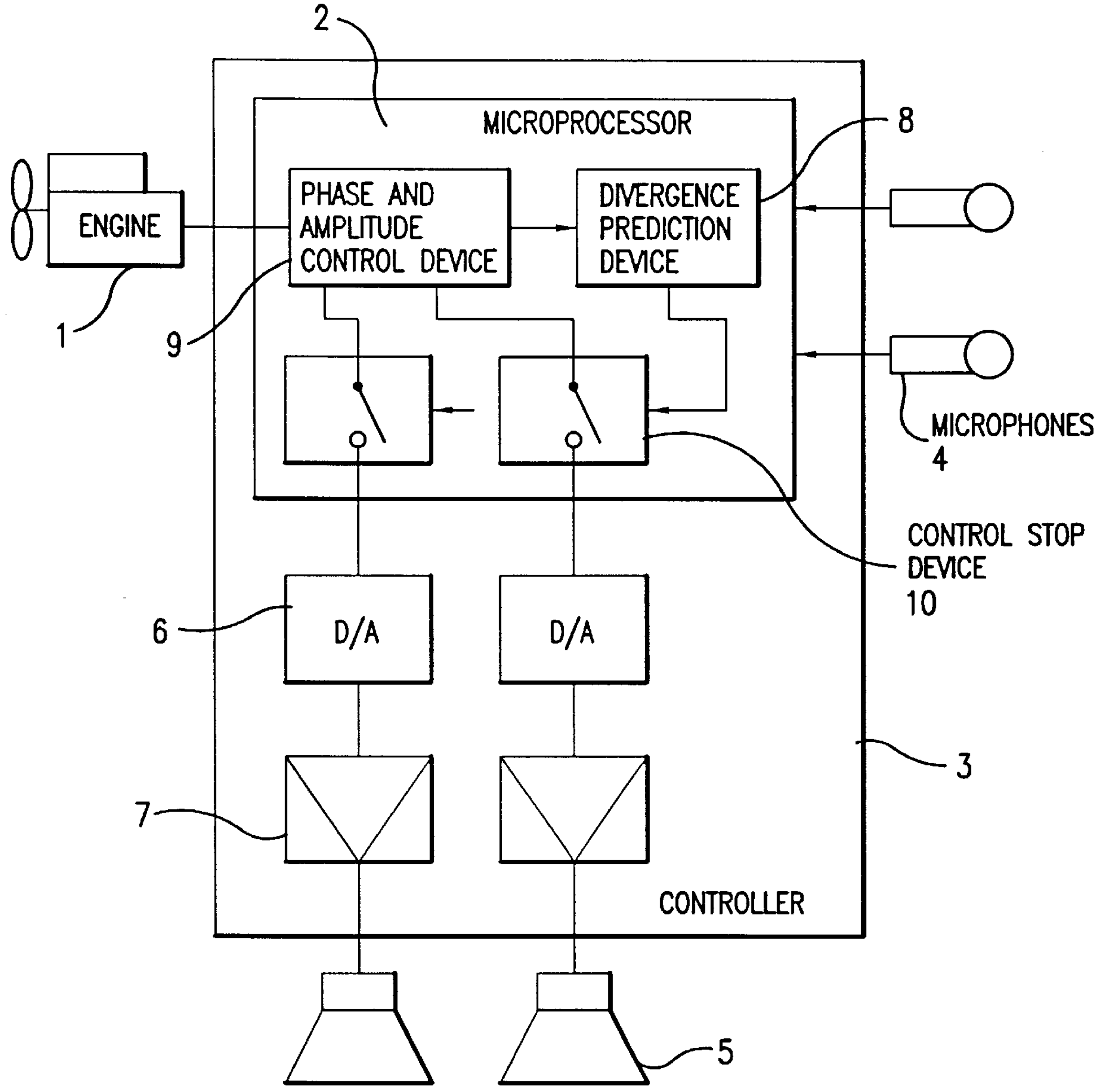
FIG. 1 is a block diagram of a noise-reducing apparatus according to an embodiment of the present invention.

FIG. 1 is a block diagram of a noise-reducing apparatus of an embodiment of the present invention. It comprises a plurality of speakers 5 as actuators for generating secondary sounds, a plurality of microphones 4 for detecting remaining noises in a noise space, and a controller 3 having a microprocessor 2 as an arithmetic unit. It also comprises a D/A converter 6 for converting a digital signal, such as an arithmetic signal, from the microprocessor 2 to an analog signal which is provided to a power amplifier 7 for amplifying the analog signal. The microprocessor 2 comprises a phase and amplitude control device 9 for making calculations in terms of the engine rotational frequencies from an engine 1, and the remaining noises provided from the microphones 4 in the noise space to calculate phases and amplitudes of the secondary sounds. The microprocessor 2 has a divergence prediction device 8 for judging whether the calculated secondary sounds are normal or are moving to an abnormal state. A control stop device 10, upon prediction of the divergence, prevents the secondary sound signals calculated by the phase and amplitude control device 9 from being transferred to the D/A converter 6.

Figure 2:
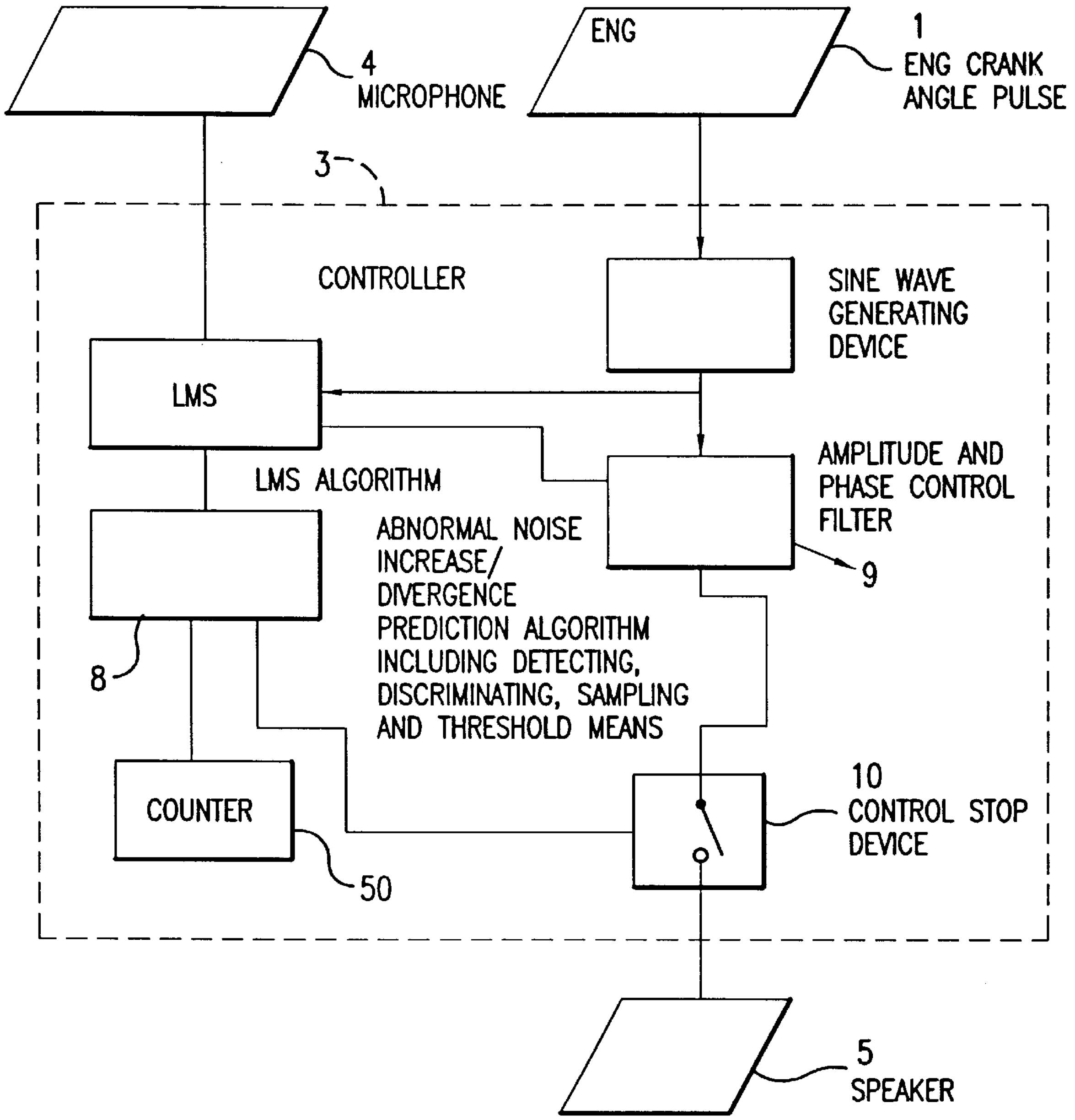
FIG. 2 is a detailed block diagram for a controller used in the embodiment of FIG. 1.

FIG. 2 is a detailed block diagram of the controller 3, with the D/A converters 6 and the power amplifiers 7 shown in FIG. 1 not shown here. In order to explain a divergence algorithm which will be described later, assume the noises to be reduced by the secondary sounds are at a single frequency due to the engine rotational frequency, which will be referred to below as the noise frequency. The phase and amplitude control device 9 of the microprocessor 2, discussed in FIG. 1 is made up of software, comprising, for example, a sine wave generator, an LMS algorithm, and a phase and amplitude control filter. Also, the divergence prediction device 8 is made up of a software divergence prediction algorithm. Further, the control stop device 10 is made up of software. One of ordinary skill in the art will recognize that the divergence prediction device 8, the phase and amplitude control device 9, and control stop device 10 can be made up of hardware instead of software.

When a crank pulse synchronized with the engine rotation is fed to the controller 3 as a reference signal, the sine wave generator converts it to a sine wave of the same frequency as the noise frequency. The noise signals, detected by the microphones 4 in the noise space, and a reference sine signal fed out of the sine wave generator are both fed to the LMS algorithm. The LMS algorithm controls coefficients of the phase and amplitude control filter so that a square summation of the noise signals should be minimized. The reference sine wave signals fed out of the sine wave generator are filtered through the phase and amplitude control filter 9. The filtered signal (secondary signal) is fed out of the speakers 5.

The LMS algorithm is used to process the sine wave generator and microphone signals to provide the filtered signal. This method is described in detail in an article by Elliot titled "A Multiple Error LMS Algorithm and Its Application to the Active Control of Sound and Vibration" published in the IEEE Transactions on Acoustics, Speech, and Single Processing, Vol. ASSP-35, No. 10, October 1987. The method is also described in the following patents: GB Patent No. 2,203,016 to Elliot et. al. titled "Active Sound Control Apparatus", GB Patent No. 2,149,614 to Nelson et.al. titled "Active Noise Reduction Apparatus", and GB Patent No. 2,201,858 to Elliot et. al. titled "Active Noise Control".

Letting X equal the sine wave generator signal, E the error signal, and Y the filtering signal, then the processing of X and E to provide Y can be expressed generally in the following equation:

$$Y=f(X,E)$$

indicating that Y, the signal that drives the speakers 5, is a function of the signal X of the engine 1 and the signal E provided by the microphones 4. One way to determine Y is to employ as the amplitude and phase control filter 9, a two term digital FIR (Finite Impulse Response) filter having filter coefficients W1 and W2. The following equation (EQ.1) illustrates such a filter:

$$Y(n)=W1 \bullet X(n)+W2 \bullet X(n-1)$$

where Y(n) and X(n) represent the present values of X and Y, respectively. X(n−1) represents a previously sampled value of X.

W1 and W2, the filter coefficients, are continuously adjusted based on the signal E. The equations (EQ.2 and EQ.3, respectively) for adjusting the filter coefficients are:

$$W1(n) = W1(n-1) + E(n) \cdot \sum_{j=0}^{J-1} C_j \cdot X(n-j)$$

and

-continued $$W2(n)=W2(n-1)+E(n)\cdot\sum_{j=0}^{J-1}C_j\cdot X(n-1-j)$$

Initial values for the filter coefficients W1 and W2 are based on a variety of functional factors known to those skilled in the art.

The term $C_j$ in the above equations represents the jth coefficient of the space acoustic transfer function that compensates for the signal distortion/delay that occurs between the speakers 5 and the microphones 4, when this space acoustic transfer function is expressed as a finite-impulse representation digital filter. J represents the total number of coefficients (taps) of the acoustic transfer function of the digital filter and is determined by a variety of functional factors known to one skilled in the art. The signal provided to the speakers 5 arrives at the microphones 4 after a delay and with some distortion/attenuation from its original form. Theoretically, therefore, $C_j$ could represent a very complicated function for modeling the response of the microphones 4 to the speakers 5. Furthermore, $C_j$ could also be made to depend upon the contents and construction of the cabin or cab. $C_j$ could also depend upon the number, position, and composition of the passengers, the state of the window (i.e. open or closed), the material used to construct the interior of the cabin or cab, etc.

However, for the embodiment of the invention illustrated herein, $C_j$, for all j's, is a constant value. In many instances, approximating $C_j$ as a constant instead of a function is valid for a wide range of operating conditions. For the present embodiment of the invention, $C_j$ is determined empirically, by means known to those skilled in the art and described in the above references, and then programmed into the microprocessor software.

A variety of conditions can cause the above described FIR filter to become unstable. For example, a sudden atmospheric temperature change can cause the physical space acoustic transfer characteristics to change abruptly. When this occurs, the amplitude and phase control filter 9 may provide to the speakers 5 a signal having a misaligned phase and/or incorrect amplitude wherein the provided signal increases, instead of decreases, the amount of undesirable noise in the cab or cabin.

Figure 3:
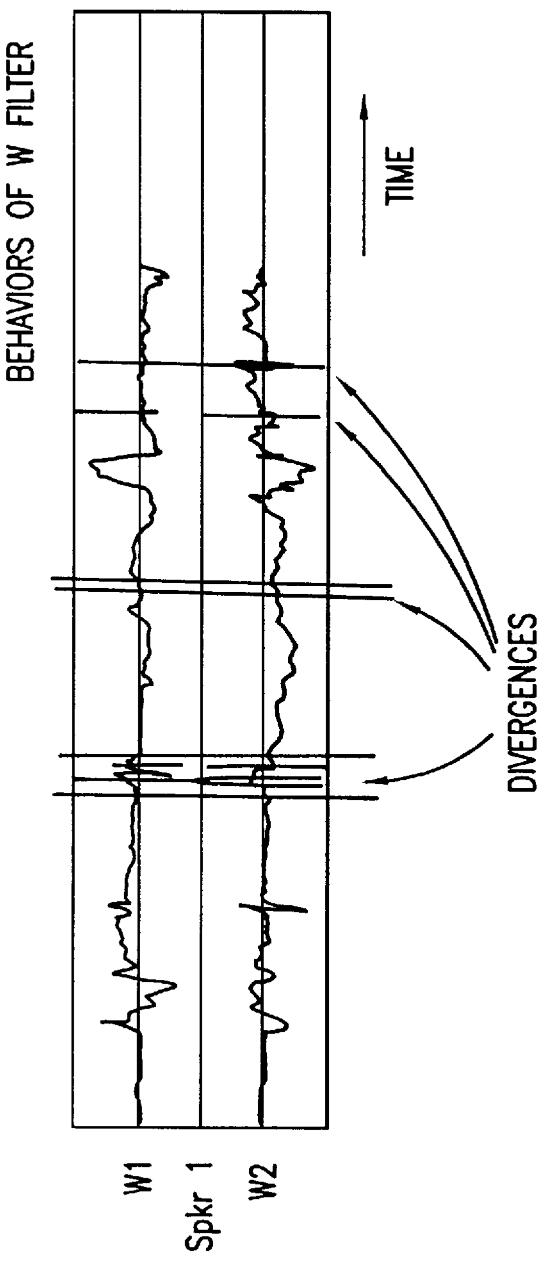
FIG. 3 is a graph illustrating behaviors of the adaptive digital filter when the noise-reducing control is made normal and when it causes the divergence.

FIG. 3 is a graph illustrating behaviors of the adaptive digital filter when the noise-reducing control is made normal and when it causes the divergence. The coefficients W1 and W2 of the adaptive digital filter, as can be seen from the graph, are within acceptable ranges while the noise-reducing control is made normal. But, they are out of these ranges when the divergence occurs. The noise-reducing apparatus according to this embodiment monitors the coefficients W1 and W2 to predict that the noise is increased with the secondary sound radiation when the coefficients W1 and W2 are out of the set ranges. Then, it interrupts the secondary sound radiation.

With the interruption of the secondary sound radiation at the first stage when the coefficients W1 and W2 increase beyond the set ranges, the noise will not actually increase. The reason is that the coefficients of the adaptive digital filter are updated at a speed over two times the frequency of the noise to be reduced. That is, in general, the coefficients are updated at a higher speed than 500 Hz for the noise frequency of 250 Hz. This makes it possible to predict whether the noise is increased (diverged) by the secondary sound radiation by monitoring whether the coefficients W1 and W2 of the adaptive digital filter are made abnormal or not. The secondary sound signal can be cut from the speaker by the control stop device 10 at the time of prediction of the divergence to prevent the speaker 5 from radiating the secondary sound before making an operator and similar persons uncomfortable.

There are many possible ways to examine W1 and W2 to determine when divergence occurs. W1 and W2 can be compared to predetermined constants and the secondary signal cut off when one or both W1 and W2 exceed those constants. Another alternative, however, is to determine the power of the signal Y by examining W1 and W2. This can be done by first writing EQ.1 in the time domain form as:

$$Y=W1\bullet\sin(\omega T)+W2\bullet\sin(\omega(\tau-T))$$

where sin ($\omega\tau$) represents X(n), sin ($\omega(\tau-T)$) represents X(n−1), and T is the sampling period.

Basic algebraic substitutions and manipulations yields the following equation:

$$Y=(W1^2+W2^2+2\bullet W1\bullet W2\bullet\cos(\omega T))^{1/2}\bullet\sin(\omega\tau+\psi)$$

where the term $Y=W1^2+W2^2+2\bullet W1\bullet W2\bullet\cos(\omega T))^{1/2}$ indicates the amplitude or power of the signal and $\psi$ indicates the phase. Note that $\psi$ equals ArcTan ((W2• sin ($\omega$T))/(W1+W2• cos ($\omega$T))).

Therefore, it is possible for the divergence prediction algorithm to calculate the power of the signal Y and to cut off the secondary signal when the power exceeds a predetermined constant. The value of the constant is based on a variety of functional factors known to those skilled in the art.

Figure 4:
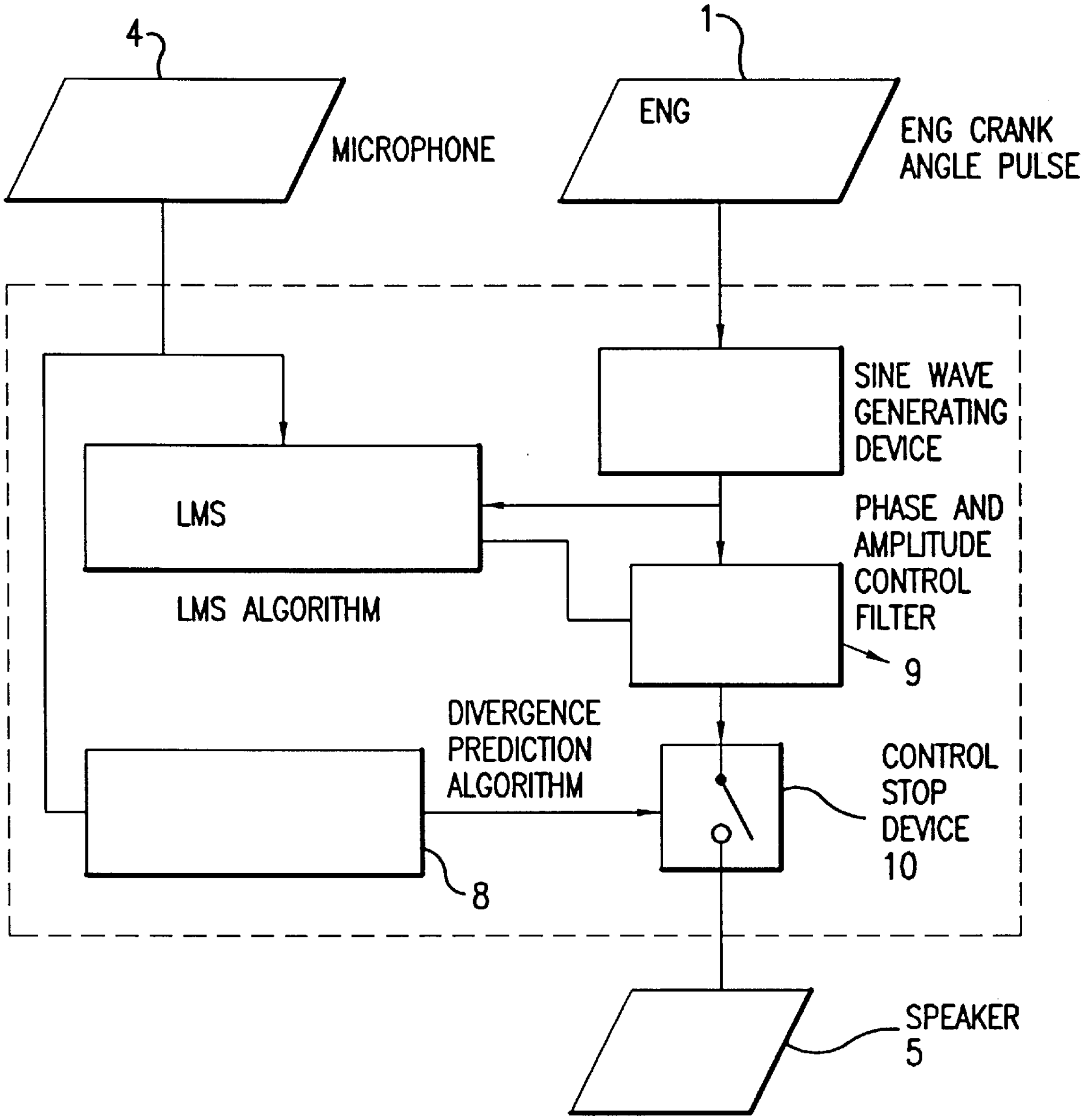
FIG. 4 is a detailed block diagram for a controller of another embodiment of the present invention for the noise-reducing apparatus.

FIG. 4 is a detailed block diagram for a controller of another embodiment of the present invention for the noise-reducing apparatus. This embodiment has a divergence prediction algorithm to predict the divergence in terms of a pressure signal of the noises detected by the microphones 4 to control the control stop device 10, while the preceding embodiment shown in FIG. 2 had the filter coefficients obtained by the LMS algorithm used to predict the divergence.

Figure 5A:
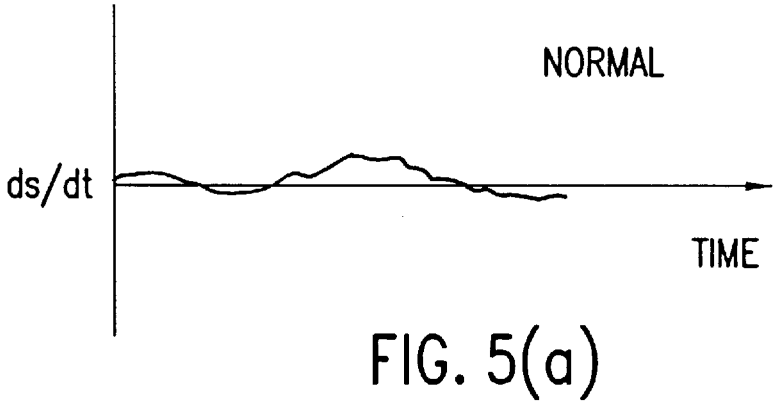
FIG. 5 are graphs illustrating the divergence prediction algorithm in terms of the signals detected by the microphones.
Figure 5B:
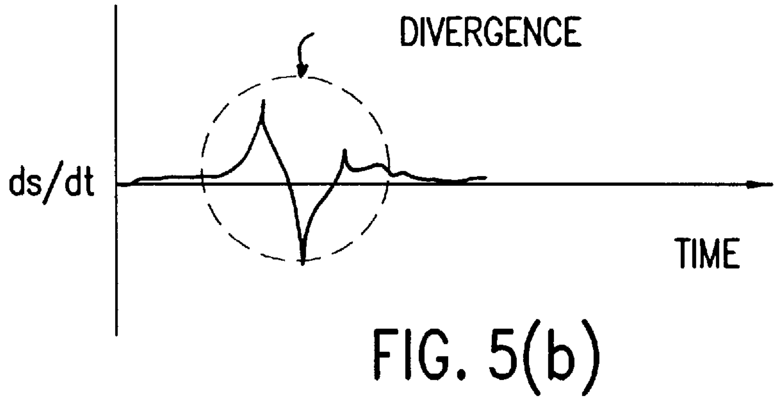

FIG. 5 includes two graphs illustrating principles of the divergence prediction in terms of the signals detected by the microphones 4. A change of the sound pressure s detected by the microphones 4, that is, a time differential ds/dt, as shown in FIG. 5(*a*), is low when the noise-reducing control is made normally. However, the time differential, as shown in FIG. 5(*b*), changes abruptly to become unstable when the divergence state occurs. This makes it possible to prevent the noise from increasing in the way that the control stop device 10 cuts the secondary sound signal from the speaker 5 when the time differential of the noise detection signal s exceeds beyond a set range as monitored.

The embodiments described above are used to reduce the noises involved in closed spaces, such as operator's cab and cabins. The present invention can also be used as a noise-reducing apparatus for reducing the noises radiated out of the cab, cabins and open spaces. It is also useful as a vibration-reducing apparatus that cancels a mechanical vibration out with a secondary vibration of the same amplitude and reverse phase as the mechanical vibration.

The noise-reducing apparatus according to the present invention can cancel the noises and mechanical vibrations out with the secondary sounds and secondary vibrations of the same amplitudes and reverse phases. It can automatically interrupt generation of the secondary sounds and secondary vibrations as it can predict the event that the noises and vibrations will be increased the worse by the secondary sounds and secondary vibrations before they become worse. It thus can always reduce the noises.

Even though the invention is illustrated herein with microphones as sound sensors and speakers as sound sources, it will be appreciated by one skilled in the art that one could use a variety of types of sound sources and/or sensors without departing from the spirit and scope of the invention. Similarly, one skilled in the art could easily adapt the invention to use any number of sound sources and/or sensors without departing from the spirit and scope of the invention. Although the invention is illustrated herein as using a microprocessor-based FIR digital filter, one skilled in the art could practice the invention with a different type of digital filter (such as an IIR filter). One skilled in the art could also practice the invention by using discrete hardware instead of a microprocessor, and/or by using analog circuitry instead of digital circuitry. The invention can be practiced without necessarily updating the filter coefficients each and every sampling period. Similarly, it is not necessary to check for divergence at every sampling period or even synchronously with updating of the filter coefficients. Also, one skilled in the art can use methods other than those illustrated herein to detect divergence of the filter without departing from the spirit and scope of the invention. One skilled in the art could practice the invention wherein $C_j$ from EQ.2 and EQ.3 represents a function rather than a constant value.

While we have shown and described an embodiment in accordance with the present invention, it is to be understood that the same is not limited thereto but is susceptible to numerous changes and modifications as known to a person skilled in the art, and we therefore do not wish to be limited to the details shown and described herein but intend to cover all such changes and modifications as are obvious to one of ordinary skill in the art.

B. Preferred embodiments of the active noise-reducing apparatus according to the present invention will now be described by reference to the drawings. While an application of the present invention to a closed space, such as, the compartment of a vehicle is taken as an example in the following description, it is apparent that the present invention is generally applicable to a closed space in an airplane, a ship, etc. besides that in a vehicle.

Figure 6:
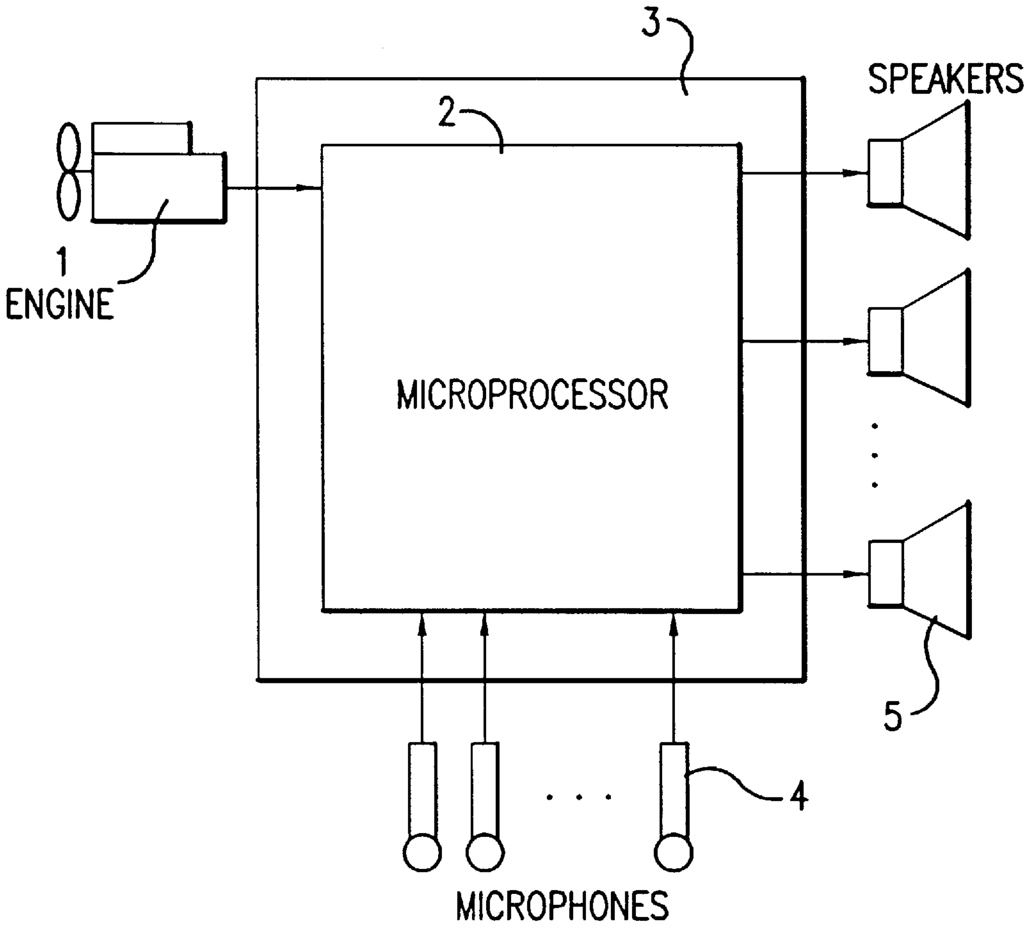
FIG. 6 PRIOR ART
FIG. 6 is a block diagram showing a conventional noise reducing apparatus.

FIG. 1 is a block diagram showing the structure of an embodiment of the noise-reducing apparatus of the present invention adapted for actively reducing noise in a vehicle compartment. In FIG. 1, like reference numerals are used to designate like parts appearing in FIG. 6. The structure of the noise-reducing apparatus of the present invention is basically similar to that of the prior art system. Referring to FIG. 1, the active noise-reducing apparatus comprises a plurality of loudspeakers 5 as actuators for generating secondary sounds, a plurality of microphones 4 for detecting residual noise in the closed space, and a controller 3. The controller 3 includes a microprocessor 2 as an arithmetic unit, D/A converters 6 converting digital input signals into analog output signals, and power amplifiers 7 respectively connected to the speakers 5 and amplifying the output signals of the D/A converters 6. The microprocessor 2 includes a phase/amplitude control section 9 for controlling both the phase and the amplitude of a noise input from an engine 1, an abnormal noise increase predicting circuit 8 connected to both the microphones 4 and the phase/amplitude control section 9 for predicting occurrence of the state of abnormal noise increase by continuously discriminating whether or not the noise-reducing control is in a normal state or in the process of transition to an abnormal state, and control stopping sections 10 connected to the outputs of the sections 8 and 9 respectively for preventing generation of abnormal sound when occurrence of the state of abnormal noise increase is predicted by the abnormal noise increase predicting section 8. In the illustrated embodiment of the present invention, the sections 8, 9 and 10 described above are provided in the form of software. However, these sections may be provided in the form of hardware.

FIG. 2 is a control block diagram illustrating the internal control functions of the controller 3. For the sake of explanation of an algorithm used for predicting the state of abnormal noise increase, it is supposed that noise to be reduced by generating secondary sound according to the present invention is at a single frequency due to the rotational frequency of the engine 1. An adaptive digital filter (referred to hereinafter as a W filter) for controlling both the phase and the amplitude of the noise input having the single frequency has two filter coefficients W1 and W2.

A pulse signal representing the engine crank angle synchronous with the rotation of the engine 1 is supplied to the controller 3 as a reference input signal, and this reference input signal is converted by the sine wave generator into a sine is wave signal having the same frequency as that of the principal component of the noise. The noise signal detected by the microphones 4 disposed in the vehicle compartment is inputted to an LMS algorithm together with the sine wave signal whose frequency is the same as that of the principal component of the noise signal. The LMS algorithm is used to control the phase/amplitude control adaptive digital filter (the W filter) so as to minimize the sum of the squares of the detected residual noise signal. After this reference sine wave signal is amplified after being filtered by the W filter, this reference sine wave signal (secondary signal) is generated from the loudspeakers 5 into the vehicle compartment.

Letting X equal the sine wave generator signal, E the residual noise signal (generally called error signal), and Y the filtering signal (secondary signal), then the processing of X and E to provide Y can be expressed generally in the following equation:

$$y=f(X,E)$$

indicating that Y, the signal that drives the loudspeakers 5, is a function of the signal X of the engine 1 and the signal E provided by the microphones 4. One way to determine Y is to employ as the phase and amplitude control filter 9, a two term digital FIR (Finite Impulse Response) filter having filter coefficients W1 and W2. The following equation illustrates such a filter:

$$Y(n)=W1(n)\cdot X(n)+W2(n)\cdot X(n-1) \quad (1)$$

where Y(n) and X(n) represent the present values of X and Y, respectively. X(n−1) represents a previously sampled value of X.

W1 and W2, the filter coefficients, are continuously adjusted based on the signal E. The equations (equation (2) and equation (3), respectively) for adjusting the filter coefficients are:

$$W1(n)=W1(n-1)+2\cdot\alpha\cdot E\ (n)\cdot\Sigma C(j)\cdot X(n-j) \quad (2)$$

and $$W2(n)=W2(n-1)+2\cdot\alpha\cdot E\ (n)\cdot\Sigma C(j)\cdot X(n-1-j) \quad (3)$$

Initial values for the filter coefficients W1 and W2 are based on a variety of functional factors known to those skilled in the art. The term Cj in the above equations represents the jth coefficient of the space acoustic transfer function that compensates for the signal distortion/delay that occurs between the loudspeakers 5 and the microphones 4, when this space acoustic transfer function is expressed as a finite-impulse representation digital filter. J represents the total number of coefficients (taps) of the acoustic transfer function of the digital filter and is determined by a variety of functional factors known to one skilled in the art.

Figure 7:
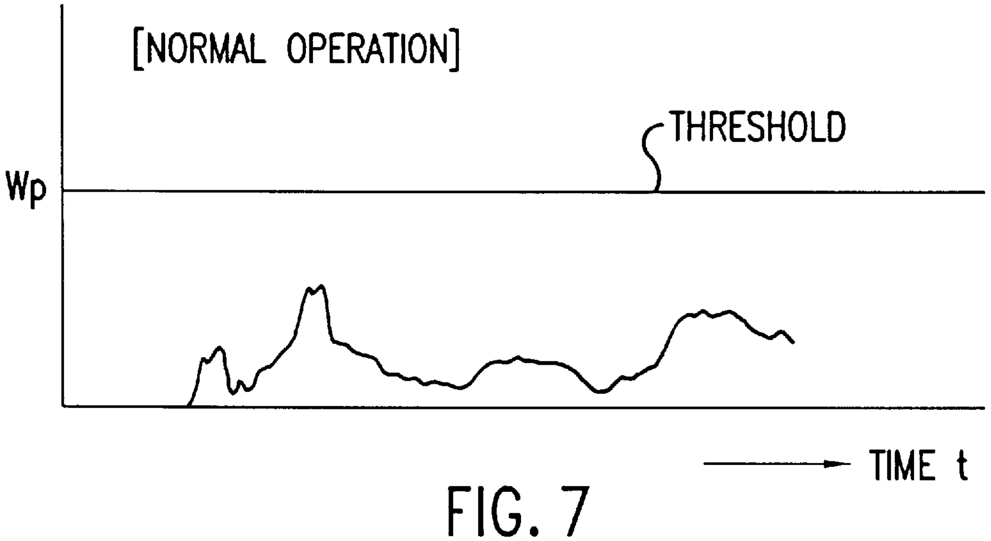
FIG. 7 is a graph showing how the output power of the digital filter changes relative to time during its normal operation.

The magnitude of the secondary sound generated from the loudspeakers 5 is proportional to the Wp calculated according to the following equation (4) using the above filter coefficients W1 and W2:

$$Wp = W1^2 + W2^2 + W1 \cdot W2 \cos \phi \qquad (4)$$

where φ phase angle determined by both the sampling frequency for the W filter and the reference signal frequency FIGS. 7 to 10 are graphs showing, by way of example, how the Wp changes relative to time under various conditions. The graph of FIG. 7 shows that the value of the Wp is in its normal range, and the magnitude of the Wp is always less than the threshold. Under the condition shown in FIG. 7, the booming noise in the vehicle compartment is effectively reduced by the secondary sound and is thus suppressed to a low level.

Figure 8:
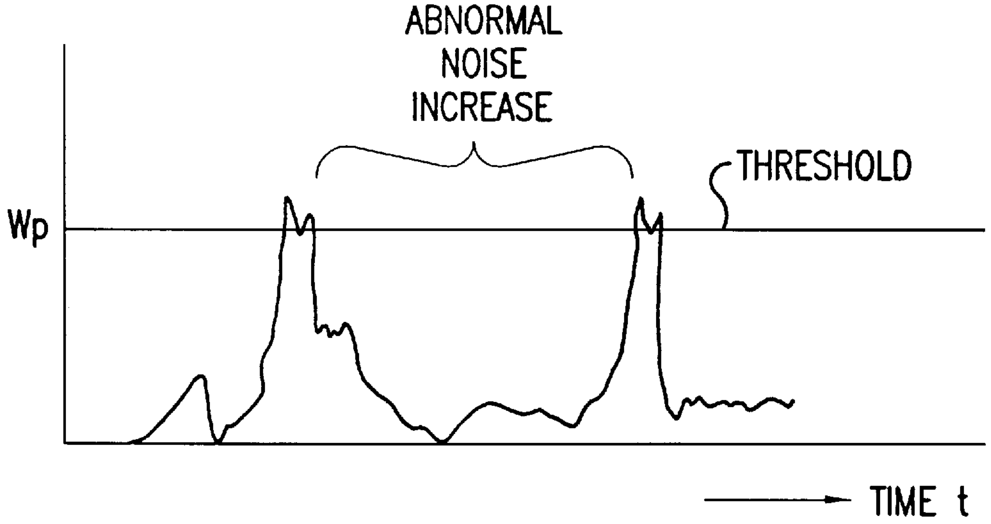
FIG. 8 is a graph showing a momentary increase in the output power of the digital filter.
Figure 9:
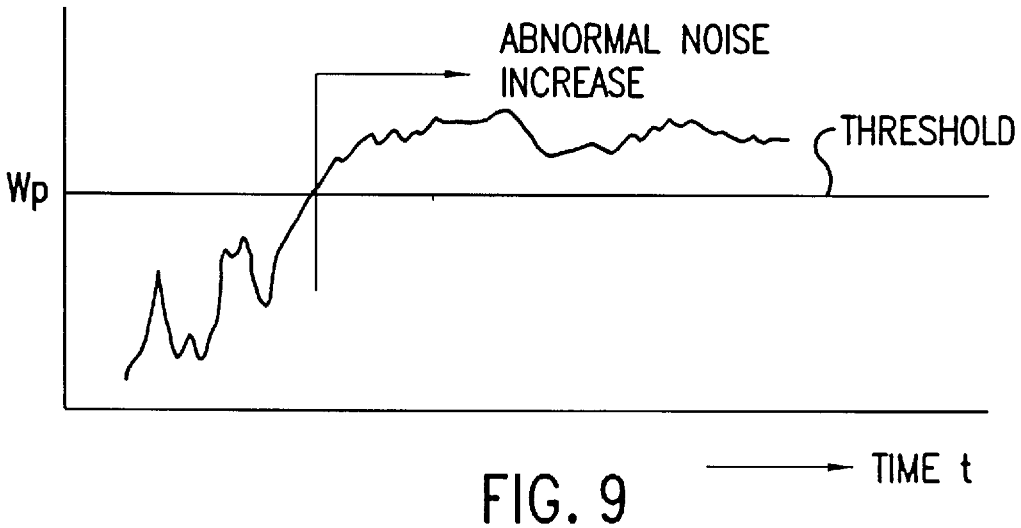
FIG. 9 is a graph showing one form of occurrence of abnormal noise increase.
Figure 10:
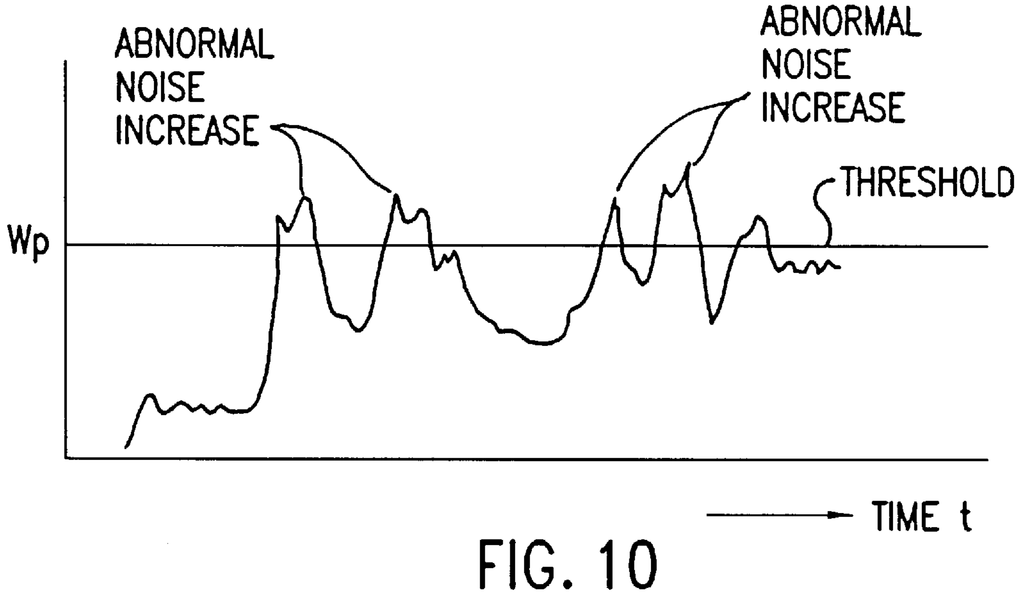
FIG. 10 is a graph showing another form of occurrence of abnormal noise increase.

When, under the condition shown in FIG. 7, the rotation speed of the engine crankshaft makes a momentary change, or other noise, for example, road noise appears besides the booming noise, the magnitude of the Wp may momentarily exceed the threshold as shown in FIG. 8. On the other hand, when the phenomenon of abnormal noise increase really occurs, the magnitude of the Wp increases, and the period of time for which the Wp exceeds the threshold becomes longer as shown in FIG. 9, or the magnitude of the Wp exceeds the threshold more frequently as shown in FIG. 10. Therefore, it is necessary to distinguish the modes shown in FIG. 9 and FIG. 10 from that shown in FIG. 8. For this purpose, the abnormal noise increase predicting section 8 continuously observes the Wp so as to continuously discriminate whether or not the value of the Wp exceeds the threshold stored in the abnormal noise increase predicting section 8. When the value of the Wp continues to exceed the threshold over a predetermined period of time, or when the total sum of time periods for which the Wp exceeds the threshold exceeds a set value, or when the ratio of this total sum to a predetermined fixed time period exceeds a predetermined value, the abnormal noise increase predicting section 8 determines the occurrence of the phenomenon of abnormal noise increase and supplies its output signal to the control stopping section 10 thereby stopping generating of the secondary sound from the loudspeakers 5.

Each time the microprocessor 2 executes its control sequence, the Wp is observed once by the abnormal noise increase predicting section 8. This control sequence is commonly carried out with timing of a predetermined sampling period. Therefore, whether or not the value of the Wp exceeds the threshold may be checked every sampling time, and, when the result of this check indicates that the threshold is exceeded, the count of the counter 50 may be incremented by one. In this manner too, occurrence of the phenomenon of abnormal noise increase can be detected when the count of the counter exceeds a predetermined count. Alternatively, it is possible to arrange the noisereducing apparatus of the invention such that occurrence of the phenomenon of abnormal noise increase is detected when the ratio of the count of the counter mentioned above to a predetermined number of times of sampling representing a predetermined fixed period of time exceeds a predetermined value.

It will be understood from the foregoing description of the present invention that the output power of the digital filter controlling the secondary sound output is continuously monitored so as to accurately predict occurrence of an undesirable phenomenon that the level of the secondary sound output becomes extremely high as compared to that of the noise to be controlled due to failure to normally carry out the noise-reducing control. Therefore, the present invention is advantageous in that the occupants of the vehicle compartment would not feel very uncomfortable due to an abnormal increase in the level of the secondary sound output.

While the invention has been particularly described and shown with reference to the preferred embodiments thereof, it will be understood by those skilled in the art that various changes in form and detail and omissions may be made therein without departing from the spirit and scope of the invention. For example, while reduction in noise of single frequency is described in the above, it is a matter of course that the present invention can be applied to reduction of noises of two or more frequencies.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A noise-reducing apparatus, comprising:

noise detection means for detecting noises generated by propagation of mechanical vibration;

arithmetic means for calculating a signal to produce secondary sounds of reverse phase to the noises in terms of frequencies of the vibrations;

secondary sound generating means for generating the secondary sounds based on the signal calculated by the arithmetic means to reduce the noises;

means for monitoring values of the signal univocally determined by adaptive filter coefficients used by the arithmetic means to calculate the signal; and means for automatically interrupting the signal before the generation of the secondary sounds if the noises and the secondary sounds at positions of the noise detection means are predicted to deviate in their reverse phase relationship or if amplitudes of the secondary sounds are predicted to deviate from amplitudes of the noises, as determined by said means for monitoring.

2. A noise-reducing apparatus, comprising:

noise detection means for detecting noises generated by propagation of mechanical vibration;

arithmetic means for calculating a signal to produce secondary sounds of reverse phase to the noises in terms of frequencies of the vibrations;

secondary sound generating means for generating the secondary sounds based on the signal calculated by the arithmetic means to reduce the noises;

means for monitoring values of the signal univocally determined by adaptive filter coefficients used by the arithmetic means to calculate the signal; and means for automatically interrupting the signal before the generation of the secondary sounds if remaining sounds of the noises and the secondary sounds at positions of the noise detection means are predicted to increase, as determined by said means for monitoring values.

3. A noise-reducing apparatus, comprising:

control means for reducing noises generated by propagation of mechanical vibration by actively canceling the noises out with secondary sounds generated by a signal calculated in terms of frequencies of the mechanical vibrations;

divergence prediction means for monitoring values of the signal univocally determined by filter coefficients used by the control means and predicting whether remaining sounds of the noises and the secondary sounds will diverge or not based on the monitored values; and function interruption means for automatically interrupting the signal and function of the control means if the divergence prediction means predicts a divergence.

4. A noise-reducing apparatus, comprising:

control means for reducing noises generated by propagation of mechanical vibration by actively canceling the noises out with secondary sounds generated by a signal calculated in terms of frequencies of the mechanical vibrations;

divergence prediction means for monitoring values of the signal functionally related to filter coefficients used by the control means and predicting whether remaining sounds of the noises and the secondary sounds will diverge or not based on the monitored values;

function interruption means for automatically interrupting the signal and function of the control means if the divergence prediction means predicts a divergence; and wherein the control means generates the signal as an output of an adaptive digital filter, and the divergence prediction means monitors coefficient values of the adaptive digital filter used to produce the signal to predict whether the remaining sounds will diverge or not.

5. A noise-reducing apparatus according to claim 3, wherein the divergence prediction means further includes means for monitoring sound pressures of the remaining sounds to predict whether the remaining sounds will diverge or not based on the monitored values and the monitored sound pressures.

6. A noise-reducing apparatus, comprising:

control means for reducing noises generated by propagation of mechanical vibration by actively canceling the noises out with secondary sounds generated as calculated in terms of frequencies of the mechanical vibrations;

divergence prediction means for monitoring values functionally related to filter coefficients used by the control means and predicting whether remaining sounds of the noises and the secondary sounds will diverge or not based on the monitored values;

function interruption means for automatically interrupting function of the control means if the divergence prediction means predicts a divergence; and wherein said monitored values include secondary sound signals fed to a secondary sound generating actuator provided in the control means.

7. Vibration-reducing apparatus, comprising:

control means for reducing mechanical vibrations propagated from a vibration source by canceling the mechanical vibrations out with secondary vibrations generated by a signal calculated in terms of frequencies of the mechanical vibrations;

divergence prediction means for monitoring values of the signal univocally determined by filter coefficients used by the control means and predicting whether synthesized vibrations of the propagated mechanical vibrations and the secondary vibrations will diverge or not based on the monitored values; and function interruption means for automatically interrupting the signal and function of the control means if the divergence prediction means predicts a divergence.

8. A noise control system, comprising:

a noise detector for detecting noise;

a counter noise generator for generating a signal to produce counter noise to reduce at least a portion of the noise detected by the noise detector, the counter noise generator including a filter with adaptive filter coefficients;

a noise divergence predictor for monitoring values of the signal univocally determined by the filter coefficients and predicting a future divergence condition with the counter noise generator contributing undesirable noise based on the monitored values; and a controller for limiting the signal before the generation of the counter noise by the counter noise generator in response to the noise divergence predictor predicting a future divergence condition.

9. A noise control system according to claim 8, wherein said controller includes a control switch for shutting off the signal from the counter noise generator in response to the noise divergence predictor predicting a future divergence condition.

10. A noise control system according to claim 8, wherein the counter noise generator includes apparatus for controlling the phase and amplitude of the counter noise being generated as a predetermined function of the phase and amplitude of the noise detected by the noise detector.

11. A noise control system according to claim 8, wherein the noise divergence predictor includes apparatus for predicting a divergence as a predetermined function of the phase and amplitude of the noise detected by the noise detector.

12. A noise control system according to claim 8, wherein the noise detector and counter noise generator are disposed in a passenger compartment of a combustion engine driven vehicle, with the passenger compartment subjected to engine induced mechanical vibrations causing the noise detected at the noise detector.

13. A noise control system according to claim 8, wherein the noise detector and counter noise generator are disposed in a passenger compartment of a combustion engine driven vehicle, with the passenger compartment subjected to sound generated by sound generation means, said sound being detected by the noise detector.

14. The noise control system of claim 8, wherein the controller automatically limits the generation of noise by the counter noise generator in response to the noise divergence predictor predicting a future divergence condition.

15. A noise control system for controlling sound in an occupant compartment comprising:

a noise detector for detecting noise;

a counter noise generator for generating a signal to produce counter noise to reduce at least a portion of the noise detected by the noise detector, the counter noise generator including a filter with adaptive filter coefficients;

a noise divergence predictor for monitoring values of the signal univocally determined by the filter coefficients and predicting a future divergence condition with the counter noise generator contributing undesirable noise based on the monitored values; and a controller for limiting the signal before the generation of noise by the counter noise generator in response to the noise divergence predictor predicting a future divergence condition.

16. A method of controlling noise in an occupant compartment of a combustion engine driven vehicle, with mechanical vibration induced noise occurring in the occupant compartment, comprising:

detecting noise in the occupant compartment at a predetermined detector location;

generating a signal to produce counter noise to reduce at least a portion of the noise of the occupant compartment by a counter noise speaker spaced from the detector location, the counter noise generator including a filter with adaptive filter coefficients;

predicting a future divergence condition in the occupant compartment during which the counter noise speaker contributes undesirable noise by monitoring values of the signal univocally determined by the filter coefficients; and automatically limiting the signal before the generation of noise by the counter noise speaker in response to the predicting of a future divergence condition.

17. In a method of reducing undesirable noise by generating a signal to produce counter noise, the step of automatically interrupting the signal before the generation of the counter noise whenever the counter noise increases the amount of undesirable noise as determined by monitoring values of the signal univocally determined by adaptive filter coefficients used in the generation of the counter noise, thereby eliminating counter noise which contributes to undesirable noise.

18. In a method of reducing undesirable noise by generating a signal to produce counter noise, the step of automatically interrupting the signal before the generation of the counter noise whenever the counter noise is about to increase the amount of undesirable noise, as determined by monitoring values of the signal univocally determined by adaptive filter coefficients used in the generation of the counter noise, thereby eliminating counter noise which contributes to undesirable noise.

19. A noise-reducing apparatus comprising:

detecting means for detecting a sound pressure of noise;

controlling means for determining an amplitude and a phase of a signal to produce secondary sound required for reducing the detected noise;

at least one loudspeaker for generating the secondary sound;

means for detecting output power of the signal, said output power being proportional to the level of a magnitude of the secondary sound generated from said loudspeaker;

means for discriminating whether or not the detected output power is higher than that of a predetermined threshold; and means for determining that an undesirable phenomenon of abnormal noise increase is occurring when the detected output power continues to exceed that of said threshold for at least a predetermined period of time, thereby to stop generating said secondary sound from said loudspeaker.

20. A noise-reducing apparatus comprising:

detecting means for detecting a sound pressure of noise;

controlling means for determining an amplitude and a phase of a signal to produce secondary sound required for reducing the detected noise;

at least one loudspeaker for generating the secondary sound;

means for detecting output power of the signal, said output power being proportional to the level of a magnitude of said secondary sound generated from said loudspeaker;

means for discriminating whether or not the detected output power is higher than that of a predetermined threshold;

means for adding together time periods for which the detected output power exceeds that of said threshold; and means for determining that an undesirable phenomenon of abnormal noise increase is occurring when the value of the time periods added by said adding means exceeds a predetermined value, thereby to stop generating said secondary sound from said loudspeaker.

21. A noise-reducing apparatus comprising:

detecting means for detecting a sound pressure of noise;

controlling means for determining an amplitude and a phase of a signal to produce secondary sound required for reducing the detected noise;

at least one loudspeaker for generating the secondary sound;

means for detecting output power of the signal, said output power being proportional to the level of a magnitude of the secondary sound generated from said loudspeaker;

means for discriminating whether or not the detected output power is higher than that of a predetermined threshold;

means for adding together time periods for which the detected output power is higher than that of said threshold; and means for determining that an undesirable phenomenon of abnormal noise increase is occurring when the ratio of the value of the time periods added by said adding means to a predetermined fixed period of time is more than a predetermined value, thereby to stop generating said secondary sound from said loudspeaker.

22. A noise-reducing apparatus comprising:

detecting means for detecting a sound pressure of noise;

controlling means for determining an amplitude and a phase of a signal to produce secondary sound required for reducing the detected noise;

at least one loudspeaker for generating the secondary sound;

means for sampling with a predetermined sampling period output power of the signal, said output power being proportional to the level of a magnitude of the secondary sound generated from said loudspeaker;

means for counting the number of times the detected output power exceeds that of a threshold; and means for determining that an undesirable phenomenon of abnormal noise increase is occurring when said count exceeds a predetermined value, thereby to stop generating said secondary sound from said loudspeaker.

23. A noise-reducing apparatus comprising:

detecting means for detecting a sound pressure of noise;

controlling means for determining an amplitude and a phase of a signal to produce secondary sound required for reducing the detected noise;

at least one loudspeaker for generating the secondary sound;

means for sampling with a predetermined sampling period output power of the signal, said output power being proportional to the level of a magnitude of the secondary sound generated from said loudspeaker;

means for counting the number of times the detected output power exceeds that of a threshold; and means for determining that an undesirable phenomenon of abnormal noise increase is occurring when the ratio of said count to that of a predetermined number of times of sampling is more than a predetermined value, thereby to stop generating said secondary sound from said loudspeaker.

24. A method of using a loudspeaker to reduce noise, comprising the steps of:

detecting a sound pressure of the noise;

determining an amplitude and a phase of a signal to produce secondary sound required for reducing the detected noise;

detecting output power of the signal, said output power being proportional to a magnitude of the secondary sound generated from the loudspeaker;

discriminating whether the detected output power is higher than that of a predetermined threshold; and determining that an undesirable phenomenon of abnormal noise increase is occurring when the detected output power continues to exceed that of said threshold for at least a predetermined period of time and ceasing generating said secondary sound from said loudspeaker in response thereto.

25. A method of using a loudspeaker to reduce noise, comprising the steps of:

detecting a sound pressure of the noise;

determining an amplitude and a phase of a signal to produce secondary sound required for reducing the detected noise;

detecting output power of the signal, said output power being proportional to a magnitude of the secondary sound generated from said loudspeaker;

discriminating whether the detected output power is higher than that of a predetermined threshold;

adding together time periods for which the detected output power exceeds that of said threshold; and determining that an undesirable phenomenon of abnormal noise increase is occurring when a value of the time periods added together exceeds a predetermined value and ceasing generating said secondary sound from said loudspeaker in response thereto.

26. A method of using a loudspeaker to reduce noise, comprising the steps of:

detecting sound pressure of the noise;

determining an amplitude and a phase of a signal to produce secondary sound required for reducing the detected noise;

detecting output power of the signal, said output power being proportional to a magnitude of said secondary sound generated from said loudspeaker;

discriminating whether the detected output power is higher than that of a predetermined threshold;

adding together time periods for which the detected output power is higher than that of said threshold; and determining that an undesirable phenomenon of abnormal noise increase is occurring when a ratio of a value of the time periods added together to a predetermined fixed period of time is more than a predetermined value and ceasing generating said secondary sound from said loudspeaker in response thereto.

27. A method of using a loudspeaker to reduce noise, comprising the steps of:

detecting a sound pressure of the noise;

determining an amplitude and a phase of a signal to produce secondary sound required for reducing the detected noise;

sampling with a predetermined sampling period output power of said signal, said output power being proportional to a magnitude of the secondary sound generated from said loudspeaker;

providing a count of a number of times the sampled output power exceeds that of a threshold; and determining that an undesirable phenomenon of abnormal noise increase is occurring when said count exceeds a predetermined value and ceasing generating said secondary sound from said loudspeaker in response thereto.

28. A method of using a loudspeaker to reduce noise, comprising the steps of:

detecting a sound pressure of the noise;

determining an amplitude and a phase of a signal to produce secondary sound required for reducing the detected noise;

sampling, with a predetermined sampling period, output power of said signal, said output power being proportional to a magnitude of said secondary sound generated from said loudspeaker;

providing a count of a number of times the sampled output power of the signal exceeds that of a threshold; and determining that an undesirable phenomenon of abnormal noise increase is occurring when a ratio of said count to that of a predetermined number of times of sampling is more than a predetermined value and ceasing generating said secondary sound from said loudspeaker in response thereto.

29. A noise-reducing apparatus, comprising:

a first detector which detects a sound pressure of noise;

a controller, responsive to said first detector, which determines an amplitude and a phase of a signal to produce secondary sound required for reducing the detected noise;

at least one loudspeaker which generates the secondary sound;

a second detector which detects output power of the signal;

a discriminator, responsive to said second detector which determines whether the detected output power is higher than that of a predetermined threshold; and a threshold detector which determines that an undesirable phenomenon of abnormal noise increase is occurring when the detected output power of the signal continues to exceed that of said threshold for at least a predetermined period of time and ceases generating said secondary sound from said loudspeaker in response thereto.

30. A noise-reducing apparatus, comprising:

a first detector which detects a sound pressure of noise;

a controller, responsive to said first detector which determines an amplitude and a phase of a signal to produce secondary sound required for reducing the detected noise;

at least one loudspeaker which generates the secondary sound;

a second detector which detects output power of the signal, said output power being proportional to a magnitude of said secondary sound generated from said loudspeaker;

a discriminator, responsive to said second detector which determines whether or not the detected output power is higher than that of a predetermined threshold;

an adder which adds together time periods for which the detected output power exceeds that of said threshold; and a threshold detector which determines that an undesirable phenomenon of abnormal noise increase is occurring when a value of the time periods added by said adder exceeds a predetermined value and ceases generating said secondary sound from said loudspeaker in response thereto.

31. A noise-reducing apparatus, comprising:

a first detector which detects sound pressure of noise;

a controller, responsive to said first detector, which determines an amplitude and a phase of a signal to produce secondary sound required for reducing the detected noise;

at least one loudspeaker which generates the secondary sound;

a second detector which detects output power of the signal, said output power being proportional to a magnitude of said secondary sound generated from said loudspeaker;

a discriminator, responsive to said second detector, which determines whether or not the detected output power is higher than that of a predetermined threshold;

an adder which adds together time periods for which the detected output power is higher than that of said threshold; and a threshold detector which determines that an undesirable phenomenon of abnormal noise increase is occurring when a ratio of a value of the time periods added by said adder to a predetermined fixed period of time is more than a predetermined value, and thereby ceases generation of said secondary sound from said loudspeaker.

32. A noise-reducing apparatus, comprising:

a first detector which detects a sound pressure of noise;

a controller, responsive to said first detector, which determines an amplitude and a phase of a signal to produce secondary sound required for reducing the detected noise;

at least one loudspeaker which generates the secondary sound;

a sampler which samples, with a predetermined sampling period, output power of the signal, said output power being proportional to a magnitude of the secondary sound generated from said loudspeaker;

a counter that provides a count of a number of times the detected output power exceeds that of a threshold; and a threshold detector which determines that an undesirable phenomenon of abnormal noise increase is occurring when said count exceeds a predetermined value and ceases generating said secondary sound from said loudspeaker in response thereto.

33. A noise-reducing apparatus, comprising:

a first detector which detects a sound pressure of noise;

a controller, responsive to said first detector, which determines an amplitude and a phase of a signal to produce secondary sound required for reducing the detected noise;

at least one loudspeaker which generates the secondary sound;

a sampler that samples, with a predetermined sampling period, output power of the signal, said output power being proportional to a magnitude of said secondary sound generated from said loudspeaker;

a counter that provides a count of a number of times the detected output power exceeds that of a threshold; and a threshold detector which determines that an undesirable phenomenon of abnormal noise increase is occurring when a ratio of said count to that of a predetermined number of times of sampling is greater than a predetermined value and ceases generating said secondary sound from said loudspeaker in response thereto.

* * * * *